US007528964B2

(12) United States Patent
Schwarz

(10) Patent No.: US 7,528,964 B2
(45) Date of Patent: May 5, 2009

(54) METHOD AND APPARATUS FOR EXAMINING SURFACES CONTAINING EFFECT PIGMENTS

(75) Inventor: Peter Schwarz, Koenigsdorf (DE)

(73) Assignee: Byk-Gardner GmbH (DE)

(*) Notice: Subject to any disclaimer, the term of this patent is extended or adjusted under 35 U.S.C. 154(b) by 0 days.

(21) Appl. No.: 11/872,427

(22) Filed: Oct. 15, 2007

(65) Prior Publication Data

US 2008/0094638 A1      Apr. 24, 2008

(30) Foreign Application Priority Data

Oct. 14, 2006    (DE) ............... 10 2006 048 688

(51) Int. Cl.
*G01B 11/30* (2006.01)
*G01V 8/00* (2006.01)

(52) U.S. Cl. .............. 356/600; 356/445; 250/559.36; 250/330

(58) Field of Classification Search ......... 356/600–601, 356/388–394, 445, 448, 339–402; 250/559.3, 250/559.36, 559.27, 223 R, 227 G; 378/46, 378/50, 84, 90

See application file for complete search history.

(56) References Cited

U.S. PATENT DOCUMENTS

| 4,705,037 | A  | * | 11/1987 | Peyman et al. | ............... 606/166 |
| 5,187,727 | A  | * | 2/1993  | Vogler et al. | ................... 378/50 |
| 5,776,785 | A  | * | 7/1998  | Lin et al.    | ..................... 436/527 |
| 6,381,303 | B1 | * | 4/2002  | Vu et al.     | ....................... 378/46 |
| 6,498,648 | B1 | * | 12/2002 | Schwarz       | ..................... 356/445 |
| 6,900,437 | B2 | * | 5/2005  | Remillard et al. | .......... 250/330 |
| 6,907,108 | B2 | * | 6/2005  | Yokhin et al. | ................. 378/84 |
| 7,120,228 | B2 | * | 10/2006 | Yokhin et al. | ................. 378/90 |
| 7,276,719 | B2 | * | 10/2007 | Schwarz       | ............... 250/559.36 |

FOREIGN PATENT DOCUMENTS

JP           06167339 A    *    6/1994

* cited by examiner

*Primary Examiner*—Sang Nguyen
(74) *Attorney, Agent, or Firm*—Hayes Soloway P.C.

(57) ABSTRACT

The present invention describes a method for an apparatus for examining surface properties. Properties of effect pigments are to be examined in particular. A surface (9) to be examined is examined at different emission and reception angles and any curvature of the effect pigments is deduced on the basis of these different angles.

23 Claims, 2 Drawing Sheets

METHOD AND APPARATUS FOR EXAMINING SURFACES CONTAINING EFFECT PIGMENTS

FIELD OF THE INVENTION

The present invention relates to a method and an apparatus for determining surface properties.

The invention will be described with reference to surfaces of motor vehicles. However, it is pointed out that the invention can also be used on other surfaces, such as for example the coatings of furniture, of floor coverings and the like.

BACKGROUND OF THE INVENTION

The optical appearance of objects or of the surfaces thereof, particularly surfaces on motor vehicles, is greatly determined by the surface properties thereof. However, since the human eye is suitable only to a limited extent for the objective determination of surface properties, there is a need for aids and apparatuses for the qualitative and quantitative determination of surface properties.

Examples of such surface properties are the gloss, orange peel, colour, macrostructure or microstructure, image sharpness, haze, surface structure and/or surface topography and the like.

Furthermore, coatings which contain so-called effect pigments are enjoying greater popularity in recent times. In these coatings, a large number of effect pigments which act like small mirrors are arranged in the paint layer. Ideally, such effect pigments have a planar surface and are arranged essentially parallel to the coating itself.

In reality, however, the surface of such effect pigments is not planar but rather may be curved for example in a concave or convex manner. As a result of this curvature, a light beam impinging on these pigments is widened or narrowed and this leads to an altered optical appearance of the surface as a whole. If such a curved effect pigment reflects radiation impinging on it, then the viewing angles at which this effect pigment can be perceived depends inter alia on the curvature of the effect pigment. This angular range will be referred to below as the angular lifetime. Other unevennesses, such as cracks, edges or in general any topographical surface defects, may also have an effect on the angular lifetime.

The object of the present invention is to achieve a more accurate objective examination of such effect pigments. This object is achieved by a method and apparatus for examining surface properties, comprising the following steps:

emitting radiation at a first predefined emission angle onto a surface to be examined;

receiving at a first reception angle at least part of the radiation emitted at the first emission angle and thrown back from the surface to be examined, and outputting a plurality of first measured values which are characteristic of the received radiation;

emitting radiation at a second predefined emission angle onto a surface to be examined;

receiving at a second reception angle at least part of the radiation emitted at the second emission angle and thrown back from the surface to be examined, and outputting a plurality of second measured values which are characteristic of the received radiation, wherein at least the first and second emission angles or the first and second reception angles are different; and carrying out a comparison between the first measured values and the second measured values.

In the method according to the invention for examining surface properties, in a first method step radiation is emitted at a first predefined emission angle onto a surface to be examined. Furthermore, at least part of the radiation emitted at the first emission angle and thrown back from the surface to be examined is received at a first reception angle, and a plurality of first measured values are output which are characteristic of the received radiation.

In a further method step, radiation is emitted at a second predefined emission angle onto the surface to be examined, and at least part of the radiation emitted at the second emission angle and thrown back from the surface to be examined is received at a second reception angle, and a plurality of second measured values are output which are characteristic of the received radiation.

According to the invention, at least the emission angles or the reception angles are different. In a further method step, a comparison is carried out between the first measured values and the second measured values.

Radiation which is thrown back will be understood to mean any radiation, in particular reflected and/or scattered radiation, which passes from the surface onto a radiation detector device. With particular preference, the radiation is light and particularly preferably light in the visible wavelength range.

The radiation that is thrown back may be composed of reflected and scattered fractions, in particular of scattered light from the surface itself and of reflected light from the individual effect pigments. Preferably, the surface to be examined is imaged onto a radiation detector device or else imaging optics are used.

Preferably, either the emission angle or the reception angle is retained and the respective other angle is changed. In this way, an observation of the surface under at least two different angles can be carried out. The emission angles and the reception angles will be defined below as angles relative to a central perpendicular line from the surface. Preferably, the plurality of measured values is an array which characterises the radiation impinging on a detector device.

If, for example, the radiation is emitted twice at the same emission angle and is received at different reception angles, it can be checked whether the recordings at different reception angles point to a specific effect pigment. The angular lifetime of this effect pigment can thus be deduced from an angular difference between these two reception angles. Preferably, the radiation is emitted at a plurality of emission angles and the radiation that is thrown back is received at one specific reception angle. Conversely, it is also possible for radiation to be emitted at just one specific emission angle and to be received at a plurality of reception angles. Finally, a plurality of emission angles and a plurality of reception angles may be used.

By virtue of this plurality of angles, it is possible to specify with a high degree of accuracy the angular range at which a given effect pigment still reflects light. In this way, a very accurate image of the curvature of these effect pigments can be obtained. Preferably, the measurement does not take place in reflection, i.e. the emission angles and the reception angles are not equal but opposite.

In addition, scatter properties or reflection properties of the effect pigments can also be examined, and in particular the extent to which specific effect pigments act as mirrors or as scattering bodies.

In a further preferred method, the radiation is received in a spatially resolved manner. In this case, for example, a radiation detector with a CCD chip is provided, which outputs a spatially resolved image of the impinging radiation. Preferably, the difference between the different emission angles or reception angles is less than 5°, preferably less than 3°, particularly preferably less than 1° and particularly preferably less than 0.5°. In this way, the curvature of the effect pigment in question can be determined in a very precise manner, and the effects of such curved effect pigments can be characterised in a very precise manner.

Preferably, at least one movable radiation detector device is used to receive the radiation thrown back from the surface and in particular the scattered radiation. This radiation detector device can be displaced over a certain angular range in order in this way to determine the angular lifetime of the individual effect pigments. In a further preferred embodiment, at least one movable radiation device is used to emit the radiation onto the surface. Here, too, the radiation device can particularly preferably be moved in the circumferential direction so that, in this way, an effect pigment can be illuminated from different angles in order thus to determine the curvature thereof. In addition, besides the curvature of the individual effect pigments, it is also possible to determine the orientation thereof with respect to the plane of the coating.

However, it is also possible to use a plurality of radiation devices which are arranged at different angles with respect to the surface, and to use on the other hand a plurality of radiation detector devices which are respectively spaced apart from one another by a small angular distance. Conversely, it is also possible to use a plurality of radiation devices which are arranged at a small angular distance from one another, and to use on the other hand a plurality of radiation detector devices which are arranged at a larger angular distance from one another, for example at a distance of 10°.

The present invention also relates to an apparatus for examining surface properties. This apparatus comprises a first radiation device which emits radiation at a first predefined emission angle onto a surface to be examined. Also provided is a first radiation detector device which receives at a first reception angle at least part of the radiation emitted onto the surface and thrown back from the latter and outputs a plurality of first measured values which are characteristic of the radiation emitted at the first emission angle and received at the first reception angle.

According to the invention, measurement means are provided which allow an emission of the radiation at a second emission angle and the reception at a second reception angle of the radiation thrown back, wherein the measurement means allow the outputting of a plurality of second measured values which are characteristic of the radiation emitted at the second emission angle and received at the second reception angle, wherein at least the two emission angles or the two reception angles are different. In this case, preferably both the radiation detector device and the measurement means allow a spatially resolved reception of the radiation thrown back from the surface.

Also provided is a comparison device which compares the first measured values with the second measured values. Again in the case of this apparatus, it can be checked whether a specific effect pigment is still perceived at different illumination and viewing angles, and thus the angular lifetime of this effect pigment can be deduced.

A comparison device is understood to mean any device which allows a comparison of at least two values. In the simplest case, this may be a display device which outputs the first group of measured values and the second group of measured values to the user, so that the latter can carry out comparisons. Preferably, however, the comparison device performs these comparisons at least partially automatically. This may be achieved for example if the abovementioned arrays of measured values are loaded into a memory and aligned with one another and then individual measured values or individual groups of measured values are compared with one another. It can thus be checked whether certain phenomena are present, such as the appearance of certain effect pigments in the different sets of measured values. Preferably, the sets of measured values are also stored with information relating to this respective beam path, that is to say in particular the respective emission and reception angles. In this way, the angular lifetime of the individual effect pigments can be deduced directly by comparing the individual sets of measured values.

It should be pointed out that the complete information regarding the angular lifetime cannot be obtained until a plurality of recordings have been carried out. In principle, there are various embodiments for configuring said measurement angles. These embodiments will be explained below on the basis of several examples.

Preferably, the measurement means comprise a second radiation device which emits radiation at the predefined second emission angle $\alpha_2$ onto the surface to be examined. In this case, therefore, the two emission angles differ and the reception angles are preferably the same.

In a further preferred embodiment, a plurality of second radiation devices or in general a plurality of radiation devices are provided which direct the radiation onto the surface to be examined. In this way, the surface is illuminated at a plurality of angles which are preferably spaced apart from one another by a small distance, and the radiation that is thrown back is observed at one specific reception angle. Preferably, the surface is illuminated by the individual radiation devices one after the other, in order in this way to avoid any temporal overlap of the measurement values respectively obtained.

Conversely, however, it is also possible to provide a plurality of radiation detector devices which receive at different predefined second viewing angles the radiation thrown back from the surface. In this way, too, the angular lifetime of the individual effect pigments can be determined.

In a further preferred embodiment, the measurement means comprise an emission angle change device which moves the first radiation device relative to the surface and in this way changes the emission angle. In this way, a predefined angular range can be scanned and thus the angular lifetime of the effect pigments can be determined. In this case, the radiation device can preferably be moved in an angular range which also allows the detection of large curvatures. Here, it is possible to change the emission angle in steps of predefined magnitude, wherein these steps may be less than 5°, preferably less than 3°, preferably less than 1° and preferably less than 0.5°.

Conversely, in a further preferred embodiment, a reception angle change device may also be provided which moves the first radiation detector device relative to the surface and in this way changes the reception angle. Both embodiments, i.e. on the one hand a displacement of the radiation device and on the other hand a displacement of the radiation detector device, can be used in the same way to determine the angular lifetime.

Preferably, the first emission angle and the second emission angle differ by less than 5°, preferably by less than 3° and particularly preferably by less than 2°. Here, however, the distance between the radiation devices and the surface is also critical.

In a further preferred embodiment, the first reception angle and the second reception angle differ from one another by less than 5°, preferably by less than 3° and particularly preferably by less than 2°.

In a further preferred embodiment, the measurement means comprise a displaceable diaphragm device. In this case, for example, the diaphragm device can be used to change the emission angle onto the surface, but it can also be used to shift the viewing angle.

BRIEF DESCRIPTION OF THE DRAWINGS

Further advantages and embodiments will emerge from the appended drawings. In the drawings.

DETAILED DESCRIPTION OF THE INVENTION

Figure 1:
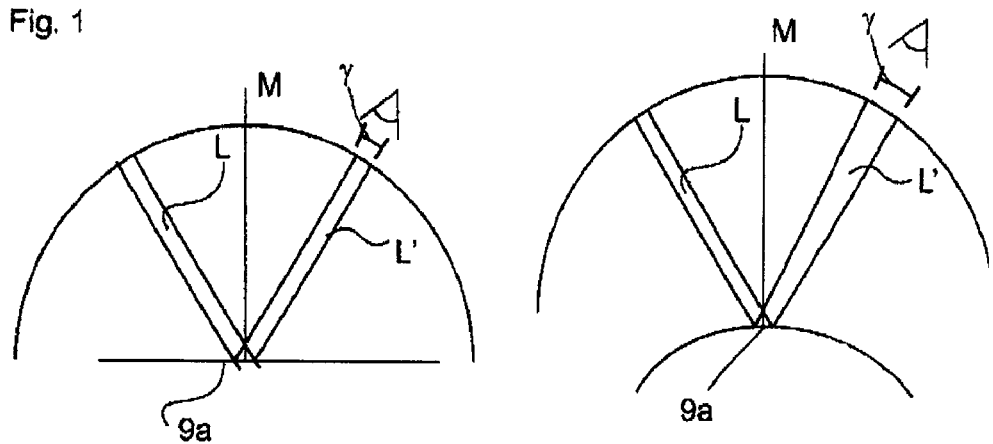
FIG. 1 shows a schematic diagram to illustrate the problem on which the invention is based.

FIG. 1 shows a schematic diagram to illustrate the problem on which the invention is based. In said figure, a light beam L is emitted onto a surface 9 or an effect pigment 9a. In the left-hand part of the figure, this effect pigment is planar, which means that the light beam is reflected by the effect pigment in a convergent manner, i.e. without being widened. If an observer looks towards the coating, he will be able to perceive the reflection from the effect pigment 9a in a predefined angular segment $\gamma$. This angular segment $\gamma$ is the aforementioned angular lifetime.

If, however, the pigment has a curved surface as shown in the right-hand part of FIG. 1, the light beam impinging on the effect pigment will be widened, as indicated by the reflected light beam L'. In this case, the angle $\gamma$ or the angular lifetime is thus increased. Conversely, the angle $\gamma$ and thus the angular lifetime would be reduced at least in the case of a slight concave curvature. The present invention makes it possible to qualify this curvature and the resulting changes in the angular lifetime. For example, it is possible to record the angular lifetime for a large number of effect pigments and to determine, from these results, mean values or variances and scatter and the like for the angular lifetime. Overall, therefore, an objective image regarding the surface occupancy can be output.

Figure 2:
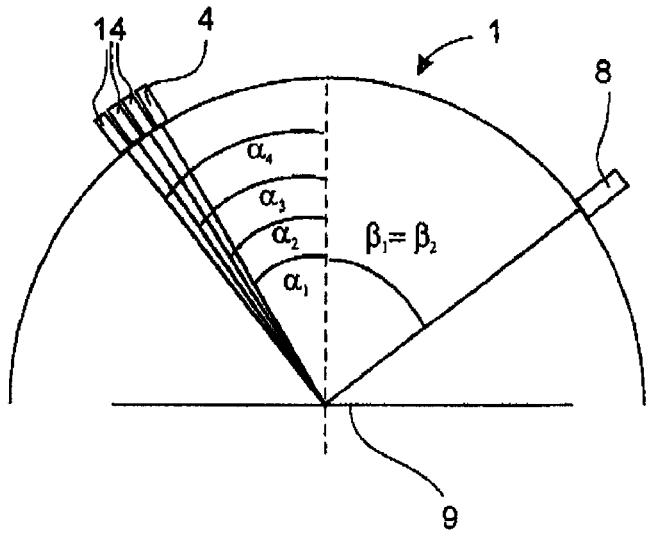
FIG. 2 shows a highly schematic diagram of an apparatus according to the invention in a first embodiment.

FIG. 2 shows a highly schematic diagram of the apparatus 1 according to the invention in a first embodiment. Here, a first radiation device 4 is provided which emits radiation at a first emission angle $\alpha_1$ with respect to the central perpendicular line M onto a surface 9 to be examined. The radiation thrown back from this surface 9 and in particular scattered by the latter is at least partially received by a first radiation detector device 8. Both the radiation device and the radiation detector device are accommodated in a housing (not shown) in order to prevent further light from outside from impinging on the surface 9. The radiation (P1) thrown back from the surface 9 is detected at a first reception angle $\beta_1$.

In addition, the apparatus comprises further radiation devices 14 which emit radiation at different emission angles $\alpha_2$-$\alpha_4$ onto the surface 9. In this embodiment, the reception angle $\beta_1$ and the reception angle $\beta_2$ are the same, and a plurality of different emission angles $\alpha_1$-$\alpha_4$ are provided. In practice, it is also possible for a considerably larger number of emission devices 14 to be provided and for these to be distributed for example over a considerably larger angular range, for example over a range of 20°.

As mentioned above, the light thrown back from the surface, which runs in the direction of the arrow L', is scattered light from the surface. The radiation detector device allows a spatially resolved recording of images or a spatial resolution of the radiation impinging thereon. As mentioned in the introduction, a large number of effect pigments are arranged in the surface, wherein these effect pigments can act like mirrors under the angular conditions presented here and can reflect the radiation onto the radiation detector device 8. In an image recorded by the radiation detector device 8, these reflected components appear as particularly bright points.

In the method according to the invention, the individual radiation devices 14 and 4 can be activated one after the other for example. Images can then be recorded in each case by the radiation detector device 8 and a check can be carried out in order to ascertain the images in which a specific effect pigment is still visible. From this information, and thus from a comparison of the individual recorded images, it is possible to determine the angular lifetime of a specific colour pigment. It is also possible to determine the angular lifetime automatically, by comparing a plurality of recorded images with one another and checking whether a specific effect pigment still appears. This measurement may also be recorded for a plurality of effect pigments. In this case, it is preferably ensured that all the radiation devices 4, 14 illuminate the same region of the surface. Furthermore, a plurality of images can be aligned by means of suitable software, for example by orientation based on specific effect pigments.

Instead of a plurality of radiation devices 4 and 14, use may also be made of a larger radiation device and a movable diaphragm device (not shown) which respectively adjusts the emission angle $\alpha_1$-$\alpha_n$.

Figure 3:
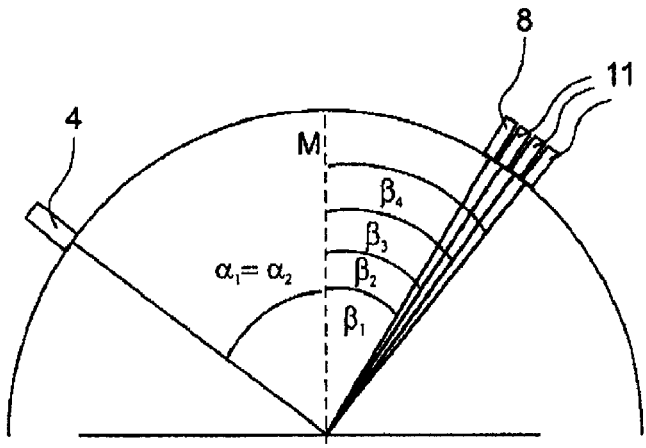
FIG. 3 shows a highly schematic diagram of an apparatus according to the invention in a second embodiment.

FIG. 3 shows a further embodiment of the present invention. In this embodiment, only one radiation device 4 is provided which emits radiation at a first emission angle $\alpha_1$, which is in this case the same as the second emission angle $\alpha_2$, onto the surface. In this embodiment, a plurality of radiation detector devices 8, 11 are provided which receive at different angles $\beta_1$-$\beta_4$ the radiation scattered by the surface. In this way, the angular lifetime of specific effect pigments can also be determined by comparing the individual angles $\beta_1$-$\beta_4$ and by looking at the respectively recorded images. In this embodiment, the recording of the individual images by the different radiation detector devices may also take place simultaneously. Furthermore, it would also be possible to provide both a plurality of radiation devices and a plurality of radiation detector devices 8, 11.

Figure 4:
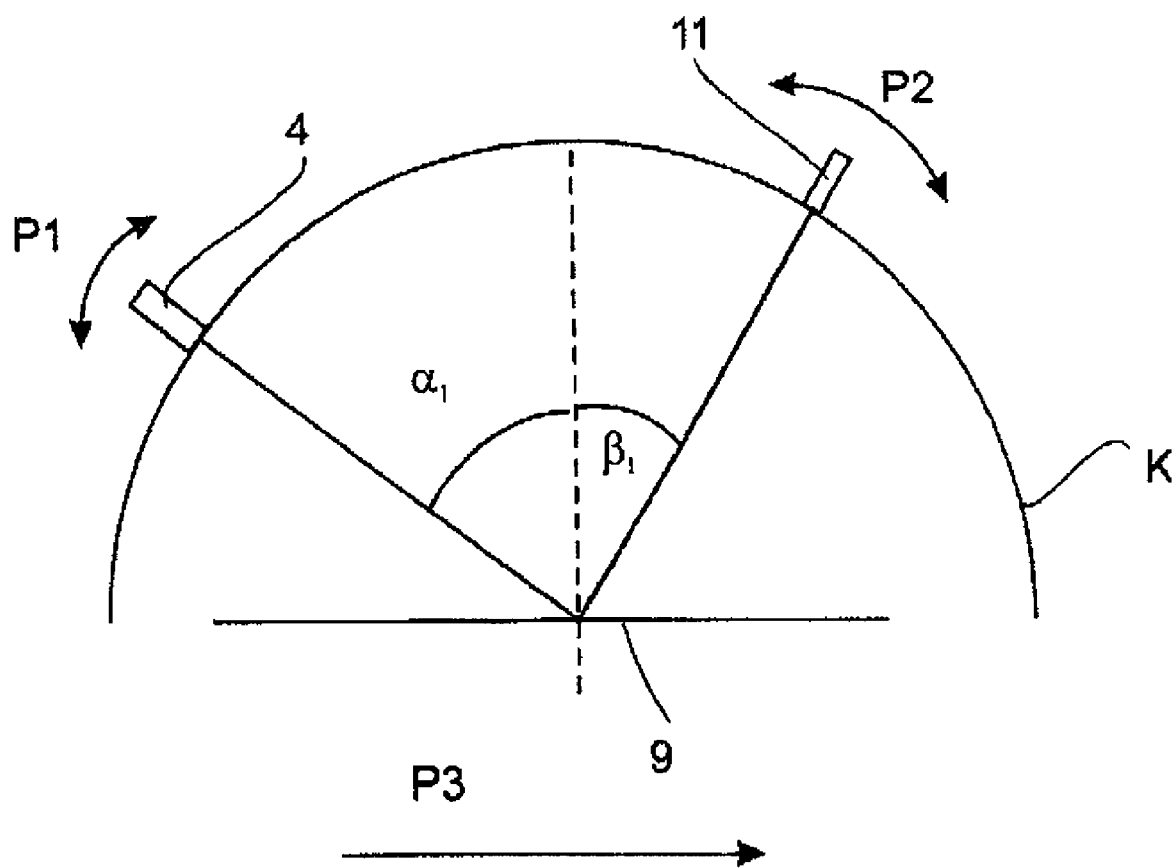
FIG. 4 shows a highly schematic diagram of an apparatus according to the invention in a third embodiment.

FIG. 4 shows a further embodiment of the present invention. In this case, just one radiation device 4 and just one radiation detector device 8 are provided. Contrary to the above embodiment, however, either the radiation device or the radiation detector device 8 can be moved along the circular line K (arrows P1, P2) in order in this way to change the emission angle $\alpha_1$ or the reception angle $\beta_1$. In the measurement method, by way of example firstly light can be emitted at the emission angle $\alpha_1$ onto the surface 9 and received at the reception angle $\beta_1$. Then either the emission direction or the radiation detector device can be displaced in order for example in a further method step to emit the light at a second emission angle $\alpha_2$ and receive it at the reception angle $\beta_1$. Conversely, it is also possible for the radiation detector device 8 to be displaced and thus for the recording to be carried out at the same emission angle $\alpha_1$ and a different reception angle $\beta_2$. However, it must be pointed out here that the emission device and the radiation detector device need not necessarily be displaced along the circular line K but rather may also be displaced in some other way, provided that the respective emission or reception angles are changed as a result. The radiation detector device 8 or the radiation device 4 may also be moved in a continuous manner in order to scan a predefined angular range.

In the method according to the invention, the entire apparatus, i.e. including all the emission devices and radiation detector devices, may be moved or displaced relative to the surface 9. Preferably, the apparatus is displaced in the direction of arrow P3 relative to the surface. It would therefore also be possible to arrange a plurality of radiation devices perpendicular to the plane of the figure in FIG. 3 and thus to measure the curvature of the individual effect pigments in a direction perpendicular to the plane of the figure. More specifically, it would be possible to arrange a plurality of radiation devices along a semicircular or hemispherical segment which extends essentially perpendicular to the plane of the figure in FIG. 3. By moving the apparatus relative to the surface, even larger surfaces can be examined with regard to their effect pigments.

Preferably, the inventive apparatus also comprises a memory device in which a large number of recorded images are stored. A comparison device can compare the individual recorded images with one another and check for example the presence of different effect pigments in the individual images in order thus to measure the angular lifetime of the respective effect pigments.

Preferably, the radiation detector device also allows coloured recording of the images, so that the effect pigments may also be different in terms of their colour. By recording and comparing a large number of images, statistical parameters for the effect pigments can also be output, for example scatter, variances or mean values for the individual curvatures.

Besides the radiation devices and radiation detector devices shown in the figures, further radiation devices may also be arranged at different angles and in particular even at very large angles. It is also possible to provide a radiation detector device at an angle $\beta_1=0$, i.e. on the central perpendicular line M. The radiation detector device 8 could also be arranged on the same side as the radiation device 4 with respect to the central perpendicular line M. In this way, it is possible in particular to detect effect pigments which are positioned extremely obliquely with respect to the surface 8. Preferably, however, the reception angle $\beta_1$ is arranged relatively close to the reflection angle $\alpha-$, for example within $+/-10°$ of this angle, since most of the effect pigments are inclined only slightly with respect to the surface 9.

It is also possible to store the recorded measured values and the recorded images of the radiation impinging on the radiation detector device and to compare these with predefined values, i.e. to catalogue them. In this way, it is possible to assign a specific surface to a surface contained in a catalogue or library and in particular to carry out a classification with regard to the quality of the effect pigments. The apparatus according to the invention and the method according to the invention can also be used to set up such libraries. Furthermore, the apparatus can also be used to carry out conventional surface measurements, for example with regard to colour, orange peel or gloss and the like. The apparatus can thus also be combined with devices known from the prior art.

It is also conceivable to use the invention with a specially adapted pigment recipe system in order to produce a specific desired pigment composition. Measured values output by the apparatus according to the invention can also be used for simulation purposes, in particular but not exclusively on a screen.

All the features disclosed in the application documents are claimed as essential to the invention in so far as they are novel individually or in combination with respect to the prior art.

LIST OF REFERENCES 1 apparatus for examining surfaces
4 first radiation device
8 first radiation detector device
9 surface
9a effect pigment
11 further radiation detector devices
14 further radiation device
Y angular segment
L light beam
L' reflected light beam
$\alpha_1, \alpha_2, \alpha_3, \alpha_4$ emission angle
$\beta_1, \beta_2, \beta_3, \beta_4$ reception angle
M central perpendicular line
P1 movement of the radiation device 4
P2 movement of the radiation detector device 8
P3 movement direction of the apparatus 1
K circular line

The invention claimed is:

1. A method for examining surface properties, comprising the following steps:
    emitting radiation at a first predefined emission angle onto a surface to be examined;
    receiving at a first reception angle at least part of the radiation emitted at the first emission angle and thrown back from the surface to be examined, and outputting a plurality of first measured values which are characteristic of the received radiation;
    emitting radiation at a second predefined emission angle onto a surface to be examined;
    receiving at a second reception angle at least part of the radiation emitted at the second emission angle and thrown back from the surface to be examined, and outputting a plurality of second measured values which are characteristic of the received radiation, wherein at least the emission angles or the reception angles are different; and
    determining the angular lifetime of an effect pigment by carrying out a comparison between the first measured values and the second measured values.

2. The method according to claim 1, wherein the radiation is emitted at a plurality of emission angles.

3. The method according to claim 1, wherein the light thrown back from the surface is received at a plurality of reception angles.

4. The method according to claim 1, wherein the radiation is received in a spatially resolved manner.

5. The method according to claim 1, the difference between the different emission angles or reception angles is less than 5°.

6. The method according to claim 5, wherein the difference between the different emission angles of reception angles is less than 3°.

7. The method according to claim 5, wherein the difference between the different emission angles or reception angles is less than 1°.

8. The method according to claim 5, wherein the difference between the different emission angles or reception angles is less than 0.5°.

9. The method according to claim 1, wherein at least one movable radiation detector device is used to receive the radiation thrown back from the surface.

10. The method according to claim 1, wherein at least one movable radiation device is used to emit the radiation onto the surface.

11. An apparatus for examining surface properties, comprising a first radiation device which emits radiation at a first predefined emission angle onto a surface to be examined, a first radiation detector device which receives at a first reception angle at least part of the radiation emitted onto the surface and thrown back from the latter and outputs a plurality of first measured values which are characteristic of the radiation emitted at the first emission angle and received at the first reception angle, wherein a measurement a device is provided which allows an emission of the radiation at a second emission angle and the reception at a second reception angle of the radiation thrown back, and wherein the measurement device allows the outputting of a plurality of second measured values which are characteristic of the radiation emitted at the second emission angle and received at the second reception angle, wherein at least the two emission angles or the two reception angles are different, and a comparison device for determining the angular lifetime of an effect pigment by allowing a comparison of the first measured values with the second measured values.

12. The apparatus according to claim 11, wherein the measurement device comprises a second radiation device which emits radiation at the predefined second emission angle onto the surface to be examined.

13. The apparatus according to claim 12, wherein the measurement device comprises a second radiation detector device which receives at the predefined second reception angle the radiation thrown back from the surface.

14. The apparatus according to claim 11, wherein the measurement device comprises a second radiation detector device which receives at the predefined second reception angle the radiation thrown back from the surface.

15. The apparatus according to claim 11, wherein the measurement device comprises an emission angle change device which moves the first radiation device relative to the surface and in this way changes the emission angle.

16. The apparatus according to claim 11, wherein the measurement device comprises a reception angle change device which moves the first radiation detector device relative to the surface and in this way changes the reception angle.

17. The apparatus according to claim 11, wherein the first emission angle and the second emission angle differ from one another by less than 5°.

18. The apparatus according to claim 17, wherein the first emission angle and the second emission angle differ from one another by less than 3°.

19. The apparatus according to claim 17, wherein the first reception angle and the second reception angle differ from one another by less than 2°.

20. The apparatus according to claim 11, wherein the first reception angle and the second reception angle differ from one another by less than 5°.

21. The apparatus according to claim 20, wherein the first reception angle and the second reception angle differ from one another by less than 3°.

22. The apparatus according to claim 20, wherein the first reception angle and the second reception angle differ from one another by less than 1°.

23. The apparatus according to claim 11, wherein the measurement device comprises a displaceable diaphragm device.

* * * * *